United States Patent [19]

Van der Knaap

[11] Patent Number: Plant 6,344

[45] Date of Patent: Oct. 18, 1988

[54] CHRYSANTHEMUM PLANT NAMED BONUS

[75] Inventor: Jacques C. M. Van der Knaap, De Lier, Netherlands

[73] Assignee: Fides Beheer B.V., De Lier, Netherlands

[21] Appl. No.: 933,089

[22] Filed: Nov. 20, 1986

[51] Int. Cl.[4] ..... A01H 5/00

[52] U.S. Cl. ..... Plt./80

[58] Field of Search ..... Plt./80

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Bonus particularly characterized by its pink double flowers, decorative flower type, excellent terminal spray, and by its adaptability to year around culture.

1 Drawing Sheet

The present invention comprises a new and distinct cultivar of Chrysanthemum, botanically known as *Chrysanthemum morifolium,* Ramat., and referred to by the cultivar name Bonus.

Bonus is a product of a planned breeding program which had the objective of creating a new chrysanthemum cultivars for use in spray mum programs having early response, pink double flowers, and the ability to produce commercially acceptable quality in year around cut mum programs. Such traits in combination were not present or needed improvement in previously available commercial cultivars.

Bonus was originated by applicant from a hybridization made in a controlled breeding program in De Lier, The Netherlands in 1981. The female parent was the cultivar Dark Flamenco. The male parent of Bonus was identified by the breeding number 79.58.

Bonus was discovered and selected by applicant as one flowering plant within the progeny of the stated parentage in June of 1982 in a controlled environment in De Lier, The Netherlands.

The first act of asexual reproduction of Bonus was accomplished when vegetative cuttings were taken from the initial selection in July of 1982 in a controlled environment in De Lier, The Netherlands by a technician working under formulations established and supervised by applicant. Horticultural examination of selected units initiated in October of 1982 had demonstrated that the combination of characteristics as herein disclosed for Bonus are firmly fixed and are retained through successive generations of asexual reproduction.

Bonus has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial practice.

The following traits have been repeatedly observed and are determined to be basic characteristics of Bonus, which, in combination, distinguish this chrysanthemum as a new and distinct cultivar:

1. Decorative flower type.
2. Pink ray florets.
3. Diameter across the face of the capitulum of 50–65 mm.
4. Good terminal spray.
5. Excellent for year around culture.

Of the many commercial cultivars known to the present inventor, the most similar in comparison to Bonus is the cultivar Pink Pompon. In comparison to Pink Pompon, Bonus has larger flowers, a different pink ray floret color, and larger leaves.

The accompanying color photographic drawing shows in front view typical inflorescence and foliage characteristics of Bonus, with colors being as nearly true as possible with illustrations of this type.

In the following description, color references are made to The Royal Horticultural Society Colour Chart. The color values were determined between 11.00 a.m. and 12:00 noon in September of 1986 under natural daylight at De Lier, The Netherlands.

Classification:

*Botanical.*—*Chrysanthemum morifolium,* Ramat., cv. Bonus.

*Commercial.*—Cut decorative spray.

INFLORESCENCE

A. Capitulum:
- *Form.*—Flat.
- *Type.*—Decorative.
- *Diameter across face.*—50–65 mm.

B. Corolla of ray floret:
- *Color (general tonality from a distance of three meters).*—Light pink.
- *Color (upper surface).*—56B near center approximately 76D near outer periphery of flower.
- *Color (under surface).*—56D.

C. Corolla of disc floret: Not relevant due to decorative form.

D. Reproductive organs:
- *Androecium.*—Not present.
- *Gynoecium.*—Present in ray florets; numerous.

PLANT

A. General appearance:
- *Height.*—80 cm.

B. Foliage:
- *Color (upper surface).*—137A.
- *Color (under surface).*—137B.
- *Shape.*—Deeply serrated.

I claim:

1. A new and distinct cultivar of chrysanthemum plant named Bonus, as described and illustrated, and particularly characterized by its pink double flowers, decorative flower type, excellent terminal spray, and by its adaptability to year around culture.

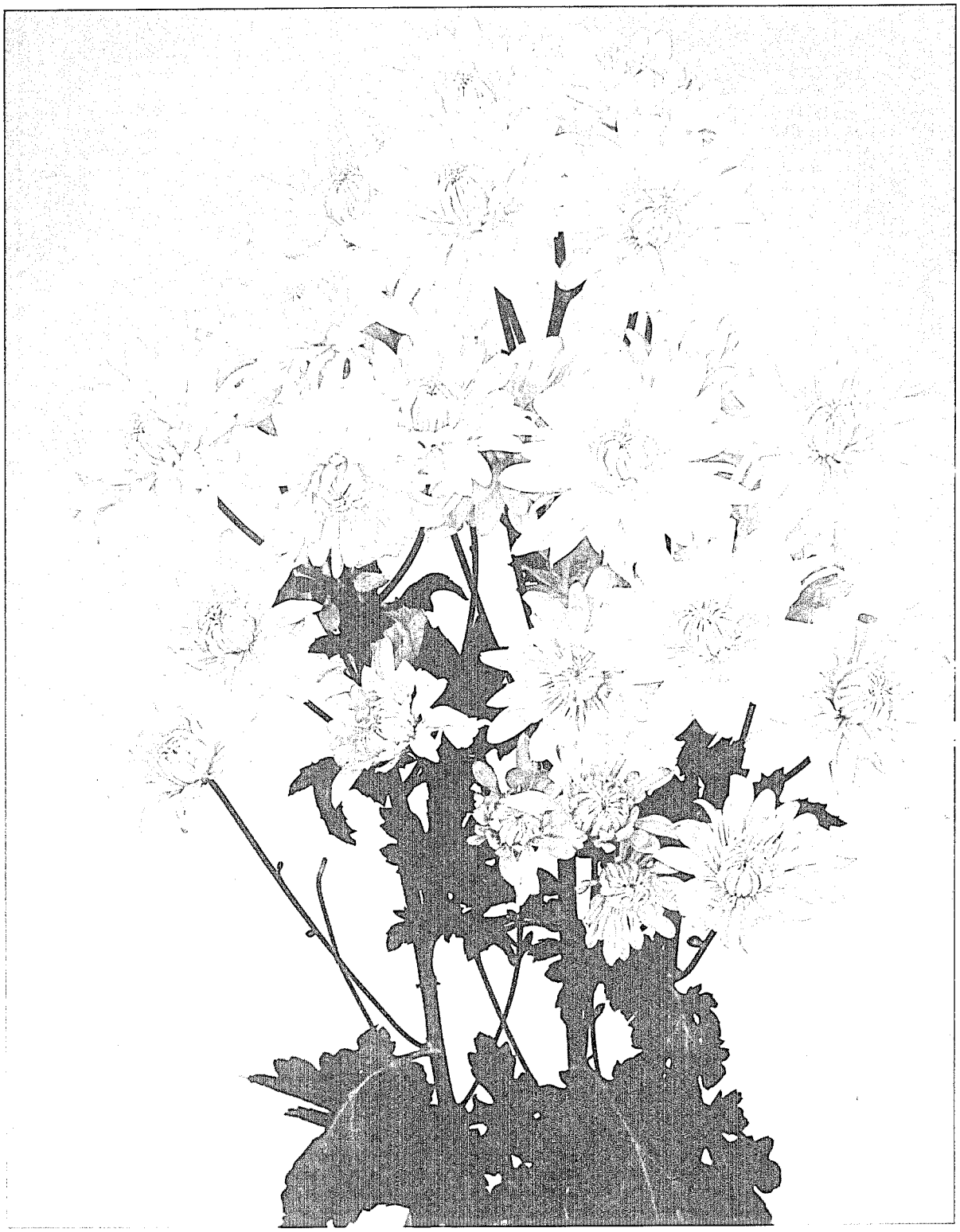

* * * * *